United States Patent [19]

Aoyama et al.

[11] Patent Number: 4,683,208
[45] Date of Patent: Jul. 28, 1987

[54] METHOD FOR THE DETERMINATION OF BILIRUBIN

[75] Inventors: Norihito Aoyama; Akira Miike, both of Shizuoka; Mikio Okano, Nagoya; Toshio Tatano, Numazu, all of Japan

[73] Assignee: Kyowa Medex Co., Ltd., Tokyo, Japan

[21] Appl. No.: 844,717

[22] Filed: Mar. 27, 1986

[30] Foreign Application Priority Data

Mar. 29, 1985 [JP] Japan .................................. 60-65600

[51] Int. Cl.$^4$ ...................... G01N 33/00; G01N 31/00
[52] U.S. Cl. ......................................... 436/12; 436/97
[58] Field of Search ..................................... 436/8–19, 436/97, 96

[56] References Cited

U.S. PATENT DOCUMENTS 4,260,579  4/1981  Barton et al. .......................... 436/12
4,405,718  9/1983  Rapkin et al. .......................... 436/12

Primary Examiner—Deborah L. Kyle
Assistant Examiner—T. J. Wallen
Attorney, Agent, or Firm—Fitzpatrick, Cella, Harper & Scinto

[57] ABSTRACT

The present invention provides a method for the determination of bilirubin which comprises reacting the bilirubin with a compound represented by the formula

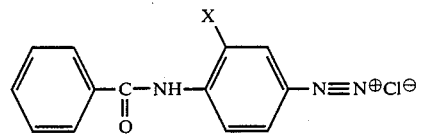

and determining the pigment thus formed.

11 Claims, No Drawings

METHOD FOR THE DETERMINATION OF BILIRUBIN

BACKGROUND OF THE INVENTION

The present invention relates to a method for the determination of bilirubin and a composition suitable therefor. Bilirubin is present in serum and the determination of bilirubin in serum is useful for the diagnosis of liver function.

With regard to the determination of bilirubin, a method using diazonium salt of sulfanilic acid is widely used. In this method, bilirubin is determined by coupling the diazonium salt of sulfanilic acid with bilirubin and determining a formed pigment colorimetrically. However, the method has the following disadvantages.

(1) It is necessary to carry out the diazotization of sulfanilic acid using a strong acid each time just before use, because diazonium salt of sulfanilic acid is unstable. Therefore, it is somewhat troublesome to perform the determination.

(2) The reaction rate of bilirubin with diazonium salt of sulfanilic acid is slow and it takes about 15 to 30 minutes to complete the reaction.

(3) It is difficult to apply the method to the determination with an automatic analyzer because a strong acid must be utilized and metals are readily corroded in the presence of the strong acid.

Thus, development of a method for the determination of bilirubin which can easily be performed without utilization of strong acid in a short period of time has been desired.

SUMMARY OF THE INVENTION

In accordance with the present invention, bilirubin can be determined by reacting bilirubin with a diazonium compound [hereinafter referred to as Compound (I)] represented by the formula

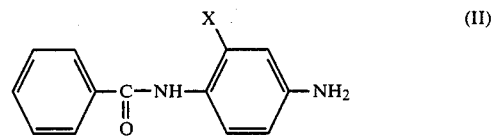

wherein X represents halogen atom to form a pigment and by determining the pigment thus formed.

Halogen atom includes chlorine, fluorine, bromine and iodine.

The present invention is based on the principle that the reaction of bilirubin in a sample with the Compound (I) proceeds stoichiometrically to form a pigment and that the amount of the formed pigment is proportional to the amount of bilirubin in the sample.

DETAILED DESCRIPTION OF THE INVENTION

In carrying out the present invention, Compound (I) is dissolved in a buffer solution having a pH in a range of 1 to 11 to prepare a reagent solution. A sample containing bilirubin is added thereto and the mixture is incubated at a temperature of 5° to 50° C., preferably 15° to 40° C. for 2 to 20 minutes.

After completion of the reaction, the absorption of the reaction solution colored by the pigment thus formed is measured at the maximum absorption wavelength of the pigment in the visible ray region on the basis of a reagent blank as a control.

Bilirubin in the sample is determined from a calibration curve obtained in advance by tests on known amounts of bilirubin.

As the buffer, hydrochloride-potassium chloride, phosphate, Tris-hydrochloride, succinate, oxalate, acetate and Good are mentioned. A surfactant such as Triton X-100 is used, if required, to clear the solution of turbidity.

Compound (I) is a known compound as an intermediate for dye synthesis which is prepared by diazotizing the compound represented by the formula (II)

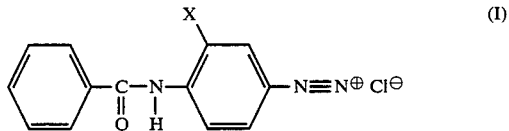

wherein X has the same meaning as defined above, which is also a known compound as an intermediate for dye synthesis.

The double salt of Compound (I) such as double salt with zinc chloride, stannous chloride, mercuric chloride and aluminium sulfate may be used as Compound (I).

It is preferred to prepare Compound (I) at the time when the determination is conducted. The preparation of Compound (I) is carried out by adding Compound (II) to a mixture of hydrochloric acid and sodium nitrite. In the reaction, Compound (II), hydrochloride and sodium nitrite are used in concentrations of 0.01–2.0 mg/ml, 0.1–5.0% and 0.1–5.0%, respectively.

The buffer solution is used in a concentration of 0.005–2 mM. Compound (I) is used in a concentration of equimolar amount or more, usually 10 to 1000 times molar to that of bilirubin in the sample. Preferable concentration is about 0.01–2.0 mg/ml.

The maximum absorption wavelength of the pigment is about 535 nm.

A composition for the determination of bilirubin in the present invention comprises Compound (I) and a buffer.

Certain specific embodiments of the present invention are illustrated in the following representative examples.

EXAMPLE 1

In 100 ml of 0.1M phosphate buffer (pH 5.0) were dissolved 500 mg of Triton X-100 and 40 mg of Compound (I) (X=Cl) to prepare a reagent solution.

Bilirubin standard solution (Daiichi Kagaku Yakuhin Co., Ltd.) was added to the reagent solution which was warmed at 37° C. in advance. After incubation at 37° C. for 5 minutes, the absorbance of the reaction solution at $\lambda_{max}$ of Compound (I) of 535 nm was measured in contrast to a reagent blank test as a control. Table 1 shows the relation between the concentration of bilirubin and the absorbance.

TABLE 1

| Concentration of bilirubin (mg/ml) | Absorbance (O.D. value) |
|---|---|
| 5 | 0.025 |
| 10 | 0.051 |
| 20 | 0.100 |

TABLE 1-continued

| Concentration of bilirubin (mg/ml) | Absorbance (O.D. value) |
|---|---|
| 40 | 0.201 |

It is evident from Table 1 that the concentration of bilirubin and the absorbance are correlated by a single straight line.

EXAMPLE 2

In 100 ml of 0.1M phosphate buffer (pH 5.0) were dissolved 500 mg of Triton X-100 and 40 mg of Compound (I) (X=Cl) to prepare a reagent solution. Five serum samples were added to (1) the reagent solution immediately after preparation (2) the reagent solution which was stored at 30° C. for 48 hours (3) the reagent solution which was stored at 37° C. for 4 hours and (4) the reagent solution which was storaged at 5° C. for a week. The mixtures were subjected to the same incubation and measurement as in Example 1. The concentrations of bilirubin in the serum samples were calculated by a calibration curve which was prepared in advance using the bilirubin standard solution.

Table 2 shows the results together with the result obtained by measuring the concentration of bilirubin in the serum samples using Bilirubin B test "Wako" (Wako Junyaku, Co.) which is a reagent for bilirubin determination.

TABLE 2

| Serum No. | Bilirubin Content (mg/dl) | | | | |
|---|---|---|---|---|---|
| | Wako | (1) | (2) | (3) | (4) |
| 1 | 0.6 | 0.6 | 0.7 | 0.6 | 0.6 |
| 2 | 0.9 | 0.9 | 0.8 | 0.9 | 1.0 |
| 3 | 0.4 | 0.5 | 0.5 | 0.4 | 0.5 |
| 4 | 1.3 | 1.4 | 1.3 | 1.4 | 1.4 |
| 5 | 0.7 | 0.6 | 0.7 | 0.7 | 0.7 |

What is claimed is:

1. A method for the determination of bilirubin in a sample which comprises reacting the bilirubin with a diazonium compound represented by the formula (I)

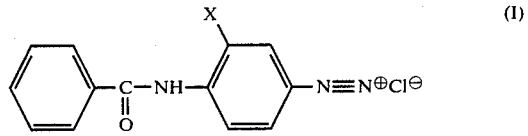

wherein X represents halogen atom and determining the formed pigment.

2. A method according to claim 1, wherein said halogen atom is a member selected from the group consisting of chlorine, bromine, iodine and fluorine.

3. A method according to claim 1, wherein said determination of pigment is carried out by photometric measurement.

4. A method according to claim 3, wherein said measurement is carried out by measuring the absorption of the reaction solution.

5. A method according to claim 4, wherein said absorption is measured in the visible ray region.

6. A method according to claim 1, wherein said reaction is carried out in a buffer solution.

7. A method according to claim 6, wherein said buffer is a member selected from the group consisting of hydrochloride-potassium chloride, phosphate, Tris-hydrochloride, succinate, oxalate, acetate and Good.

8. A method according to claim 1, wherein said reaction is carried out in the presence of surfactant.

9. A method according to claim 8, wherein said surfactant is Triton X-100.

10. A method according to claim 1, wherein said Compound (I) is used in a double salt form.

11. A composition for the determination of bilirubin which comprises a buffer and a diazonium compound represented by the formula

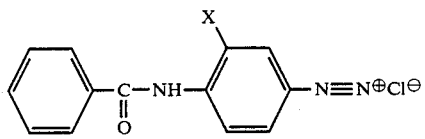

wherein X represents a halogen atom.

* * * * *